United States Patent [19]
Mori

[11] Patent Number: 5,695,779
[45] Date of Patent: Dec. 9, 1997

[54] RELEASE CONTROLLED TRANSDERMAL THERAPEUTIC SYSTEM

[75] Inventor: Masao Mori, Toyama, Japan

[73] Assignee: Lead Chemical Co., Ltd., Toyama, Japan

[21] Appl. No.: 638,565

[22] Filed: Apr. 26, 1996

[30] Foreign Application Priority Data

Apr. 28, 1995 [JP] Japan .................. HEI 7-129305
Mar. 15, 1996 [JP] Japan .................. HEI 8-087646

[51] Int. Cl.$^6$ .................................................. A61F 13/02
[52] U.S. Cl. .................... 424/448; 424/449; 424/485; 424/489
[58] Field of Search .............................. 424/448, 449, 424/485, 489

[56] References Cited

U.S. PATENT DOCUMENTS 4,573,996  3/1986  Kwiatek .................. 604/897
4,687,481  8/1987  Nuwayser ................ 604/897

FOREIGN PATENT DOCUMENTS

B2-38569   8/1990  Japan .................. A61K 9/70
3-163013   7/1991  Japan .................. A61K 9/50
4-503810   7/1992  Japan .................. A61K 31/565

*Primary Examiner*—D. Gabrielle Phelan
*Attorney, Agent, or Firm*—Oliff & Berridge

[57] ABSTRACT

A release controlled transdermal therapeutic system having excellent storage stability and capable of optionally controlling the release rate of drugs, comprising a rubbery adhesive, microcapsules comprising a water-soluble wall material and encapsulating drugs as core material, and a water-insoluble, rubber- and rubber solvent-insoluble, water absorbing resin powder, such as starch-polyacrylic acid salt copolymers, the microcapsules and the resin powder being dispersed in the rubbery adhesive.

11 Claims, 2 Drawing Sheets

RELEASE CONTROLLED TRANSDERMAL THERAPEUTIC SYSTEM

FIELD OF THE INVENTION

The present invention relates to a transdermal therapeutic system in which the release rate of drugs can optionally be controlled according to the purposes of therapeutics, having extremely excellent in storage stability, and also having high safety, being free from dermatitis or the like due to adhesion of the preparation.

BACKGROUND OF THE INVENTION

Adhesive preparations comprising natural or synthetic rubber type adhesives as a main component have disadvantages where changes on preparation, such as a decrease in drug content due to decomposition and volatilization of the drugs and a decrease in adhesive strength, are liable to occur, and storage stability of the preparation is poor.

Further, since the rubber-type adhesives do not absorb moisture, preparations comprising such adhesives may cause perspiration, or a peel off from a skin tends to occur when the skin has a high moisture at the time of adhesion. Also, in the case where the preparation has a high sealing property, dermatitis may be caused on the skin due to sodden state on the skin. Where the adhesive has less air permeability or no permeability when the adhesive preparation is used, corneous cells at the adhered portion are sealed, resulting in sodden and perhydrated state due to the moisture of skin. On the other hand, since dried skin surface layer is brittle, the skin peels at the portion where the surface layer is weakened upon peeling off the adhesive preparation from the skin. If the adhesive preparation is repeatedly adhered to the same portion under such a state, a corneous layer is destroyed, and erythema is caused due to expansion of blood vessels to cause an eruption, resulting in dermatitis. Further, the conventional transdermal therapeutic systems have disadvantages that they are well adhered to the dried and less fatty skin of old person, but have a low adhesive force to a fatty skin or a wet skin.

As a transdermal therapeutic system containing microcapsule, JP-B-2-38569 (Japanese patent publication: Hei 2-28569) proposes a system in which microcapsules that contain as a core material an absorption accelerator are dispersed in an adhesive layer, and a wall material thereof swells by skin moisture upon the adhesion to the skin, thereby the absorption accelerator diffuses into the adhesive layer. As a result, transdermic absorption of drugs contained in the adhesive layer is accelerated. In the above invention, it is believed that since skin moisture is not absorbed in a synthetic rubber type adhesive layer which is hydrophobic, the microcapsules to be swollen are restricted to the only microcapsules which are on the surface of the adhesive layer, and also since drugs are dispersed or dissolved in the adhesive layer, the system is poor in the storage stability by the mutual action between the drug components.

JP-A-3-163013 (Japanese Patent Laid Open Hei-163013) proposes an antipruritic microcapsule containing drugs as a core material and having a wall material comprising formalin resin as a main component. In the invention described in JP-A-3-163013, it is believed that the system has a high safety, but the wall material must be broken by physical friction from the outside.

PCT Publication Hei 4-503810 proposes a transdermal therapeutic system having microreserver materials of estrogen dispersed therein, but it is not believed that destruction of wall material and also diffusion of the core material are sufficient.

In those prior arts, the system has a poor storage stability, and it is impossible to control a release rate of the drugs.

The requirements for an excellent medical adhesive preparation include that the decreases in drug content and in adhesive strength do not occur, the storage stability is excellent, a moderate adhesive strength is maintained upon the adhesion even to a wet skin due to sweat or the like, and a skin is not damaged when peeling off the preparation.

It is desirable for the transdermal therapeutic system, particularly important requirements, to have a high drug absorbability and to be able to control a release rate of the drug according to the purposes of therapeutics.

SUMMARY OF THE INVENTION

Various studies have been made to overcome the problems in the conventional system that use a natural or a synthetic rubbery adhesive, and an object of the invention is to develop an excellent transdermal therapeutic system the release amount of which can optionally be controlled.

As a result, it has been found in the present invention that an adhesive preparation having high storage stability can be obtained by dispersing in a rubbery adhesive in a transdermal therapeutic system using the rubbery adhesive, microcapsules comprising water-soluble wall material and encapsulating drugs or drugs and an absorption accelerator as core material, so that the drugs are separated from the rubbery adhesive.

It has also been found that a release rate of drugs can optionally be controlled by mixing several kinds of microcapsules having different wall thickness and particle size distribution. Further, it has been found that the problems involved in the conventional rubbery adhesive can be overcome by dispersing water-insoluble, rubber- and rubber solvent-insoluble, water absorbing resin powder, and water-soluble resin powder in the adhesive to absorb sweat secreted from the skin when adhering the adhesive.

The release amount and the release rate of the drugs from the microcapsules dispersed in the rubbery adhesive depend on the concentrations of microcapsules, water absorbing resin powder and water-soluble polymer powder, the thickness of the wall material of a microcapsule, the size of a microcapsule particle, and the like, and are adjusted by controlling those factors.

In particular, the release amount and the release rate of the drugs with the passage of time are controlled by using a mixture of microcapsule particles having different wall material thickness and/or microcapsule particles having different particle size distribution.

According to a first embodiment of the present invention, there is provided a release controlled transdermal therapeutic system comprising a rubbery adhesive, microcapsules comprising a water-soluble wall material and encapsulating drugs as core material, and a water-insoluble, rubber- and rubber solvent-insoluble, water absorbing resin powder, the microcapsules and the resin powder being dispersed in the rubbery adhesive.

According to a second embodiment of the present invention, there is provided a release controlled transdermal therapeutic system comprising a rubbery adhesive, microcapsules comprising a water-soluble wall material and encapsulating drugs as core material, a water-insoluble, rubber- and rubber solvent-insoluble, water absorbing resin powder, and a water-soluble polymer powder having adhesion in the presence of moisture, the microsapsules, the resin powder and the polymer powder being dispersed in the rubbery adhesive.

According to a third embodiment of the present invention, there is provided a release controlled transdermal therapeutic system comprising the release controlled transdermal therapeutic system of the above first or second embodiment which further comprises at least two or more kinds of microcapsule particles having different wall material thicknesses and/or at least two or more kinds of microcapsule particles having different particle size distributions which are mixed therewith.

The present invention also relates to a tape preparation or a patch type adhesive preparation using those systems.

DETAILED DESCRIPTION OF THE INVENTION

Figure 1:
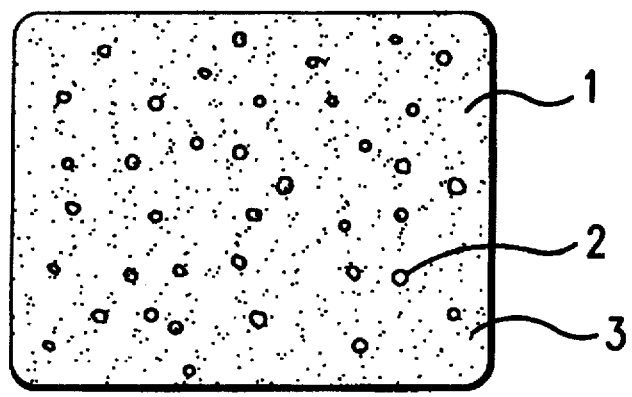
FIG. 1 is an explanatory view of a adhesive layer in a tape preparation according to the present invention.

The transdermal therapeutic system according to the present invention makes it possible to increase the storage stability of the system and to optionally control the release rate of drugs by microencapsulation of drugs, or drugs and an absorption accelerator.

When adhering the transdermal therapeutic system, a water absorbing resin powder dispersed in the adhesive absorbs body fluid such as sweat inside the adhesive to remove the retention of egesta such as sweat at the interface between the skin and the adhesive, thereby peeling off from the skin surface rarely occurs. Simultaneously, the water-soluble wall material of the microcapsules is destroyed by the absorbed moisture, and drugs, or drugs and absorption accelerator, contained in the microcapsules, are eluted and diffused in the adhesive. Further, the water-soluble polymer powder dispersed in the base material has a function to impart a adhesive properties to a system in the presence of water, and as a result, a transdermal therapeutic system which does not peel stratum corneum and is difficult to cause dermatitis can be obtained.

In the site sealed by the adhesive preparation of the present invention, the stratum corneum softens and swells, thereby a barrier property of the site is decreased, and consequently, transdermic absorption of drugs is markedly increased.

The rubbery adhesive used in the present invention comprises a rubber adhesive component, a tackifier component, and a plasticizer component.

Examples of the rubbery adhensive component that can be used in the present invention include natural rubbers; isoprene rubbers; styrene copolymer rubbers such as isobutylene rubbers, styrene-butadiene rubber, styrene-butadiene-styrene block copolymer, or styrene-isoprene-styrene block copolymer; silicone rubbers; and acrylic rubbers. Those rubbers can be appropriately selected, and can also be used alone or as a mixture of two or more thereof.

Examples of the tackifier component that can be used in the present invention include petroleum resins, rosins, hydrogenated rosins, ester gums, terpene resins, modified terpene resins, coumarone-indene resins, petroleum cracking fractions, aromatic hydrocarbon resins, styrene resins and isoprene resins. Those can appropriately be selected, and also can be used alone or as a mixture of two or more kinds thereof.

The amount of the tackifier component used is from 40 to 200 parts by weight, and preferably from 60 to 100 parts by weight, per 100 parts by weight of the rubber adhesive component.

Examples of the plasticizer component that can be used in the present invention include polybutenes, low molecular weight poly-isobutylenes, vaseline, lanolin, liquid paraffin, higher fatty acid esters, vegetable oils, and animal oils. Those can appropriately be selected, and also can be used alone or as a mixture of two or more thereof. In the present invention, low molecular weight poly-isobutylene represents semi-solid or liquid poly-isobutylene, such as "VISTANEX LM" produced by Exxon Chemical Company. Further, higher fatty acid esters represent esters formed from fatty acids having more than 11 carbon atoms, especially fatty acids having 16–18 carbon atoms, such as palmitic acid, stearic acid, oleic acid, linoleic acid and linolenic acid.

The amount of the plasticizer component used is from 30 to 300 parts by weight, and preferably from 70 to 250 parts by weight, per 100 parts by weight of the rubber adhesive component.

Natural rubbers and synthetic rubbers used for the rubber adhesive component have unsaturated bonds in the molecule, and, therefore, have the possibility to deteriorate upon exposure to oxygen or ultraviolet rays. Therefore, it is preferred for the rubbery adhesive to contain stabilizers such as antioxdant, UV absorber and the like, for example, dibutylhydroxyphenyl, or 4-ethyl-6-butylphenol.

In the present invention, drugs are mixed with and dispersed in the rubbery adhesive in the form of microcapsules.

The drugs that can be used in the present invention are oily materials that do not dissolve the wall material. Examples of the drugs that can be used include methyl salicylate, glycol salicylate, 1-menthol, dl-menthol, dl-camphor, d-borneol, peppermint oil, cayene pepper extract, vanyllamide nonylate, diphenhydramine salicylate, nitroglycerin, isosorbide dinitrate, flurbiprofen, ketoprofen, indomethacin, loxoprofen sodium, lbuprofen, dichlofenac, mefenamic acid, chrorpheniramine d-maleate, chrorpheniramine dl-maleate, diphenhydramine salicylate, diphenhydramine, progesterone, testosterone, estriol, estradiol, ethynyl estradiol, propranolol, tolubuterol, scopolamine, tranilast, ketotifen fumarate, bectometanone propionate, atropine, and lidocaine. Those can appropriately be selected, and also can be used alone or as a mixture of two or more kinds thereof. Further,the drugs are not limited to the materials as described above.

The wall material of the microcapsules comprises a water-soluble polymeric material. Examples of the wall material of microcapsules include gelatin, gum arabic, polyvinyl alcohol, and carboxymethyl cellulose. Those can be used alone or as a mixture of two or more kinds thereof. The wall thickness of the microcapsules is adjusted by changing the preparation conditions such as a mixing ratio of a core material and the wall material, a curing time of the microcapsules, thereby the release rate of drugs from the system can be controlled. Further, the release rate of the drugs can optionally be controlled by mixing two or more kinds of microcapsules having different wall thickness.

If the particle size of the microcapsules is too small, the amount of the drugs to be contained in the microcapsule decreases. On the other hand, if the particle size of the microcapsule is too large, destruction of the microcapsule particles occurs in the steps, which are mixing the particles with the adhesive, applying the resulting mixture to a base fabric, and drying the coated mixture. Also, the stability of the system cannot be obtained. Therefore, the particle size of the microcapsule is preferably in the range of from about 1 to 100 µm.

Similarly, if the wall thickness of the microcapsule is less than 0.2 µm, the microcapsules are liable to destroy, and on the other hand, if the wall thickness is larger than 2 µm, it is difficult to destroy the microcapsule film (wall of microcapsule), and solution of the core material from the microcapsule becomes slow. Therefore, the wall thickness of the microcapsule is preferably in the range of from about 0.2 to 2 µm. Further, the weight proportion of the core material in the microcapsule is preferably from 85 to 90%.

Microcapsules having various particle sizes and wall thicknesses can be obtained by adjusting microcapsules in the way such that one polymeric material or a mixture of two or more polymeric materials is used, and that conditions such as types of the core material and the wall material, the mixing ratio thereof, gelation time of the microcapsules are changed. It is possible to desirably control the release rate of the drugs by mixing two or more thus obtained microcapsules having different particle sizes and different wall thickness. That is, the microcapsules having a small wall thickness are easily destroyed by a slight amount of moisture absorption after adhesion, and the release of the drugs becomes fast. On the other hand, the microcapsules having a large wall thickness results in slow release of the drugs. Therefore, it is possible to optionally control the release rate of the drugs by adjusting the wall thickness of the microcapsules according to the purposes of therapeutics.

The core material of the microcapsule comprises drugs, and can further comprises an absorption accelerator. By containing the absorption accelerator, systems having excellent storage stability and high drug absorption property can be obtained.

The absorption accelerator that can be used in the present invention is materials that do not dissolve the wall material. Examples of the absorption accelerator include aliphatic alcohols having 10 to 22 carbon atoms, aliphatic carboxylic acids having 9 to 22 carbon atoms, aliphatic amines, long chain aliphatic esters, N-alkyllactum, crotamiton, and monoterpene compounds. Those compounds are appropriately selected, and also can be used alone or as a mixture of two or more kinds thereof.

Examples of the water absorbing resin powder that can be used in the present invention include starch-polyacrylate graft copolymer ("SUNWET", a product of Sanyo chemical Industry Co.), crosslinked polyacrylates ("ARASOAP", a trade name, a product of Arakawa Chemical Industry Co.; "AQUAKEEP", a trade name, a product of Seitetsu Chemical Industry Co.; "AQUALICK", a trade name, a product of Nippon Shokubai Chemical Industry Co.), acrylic acid-vinyl alcohol copolymers ("SUMIKAGEL S TYPE", a trade name, a product of Sumitomo Chemical Co.), polyethylene oxide crosslinked product ("SUMIKAGEL R TYPE", a trade name, as product of Sumitomo Chemical Co.), and crosslinked isobutylene-maleate copolymer ("KIGEL", a trade name, a product of Kuraray Co. ).

Those water absorbing resins are resins having three-dimensional structure obtained by appropriately crosslinking water-soluble resins. Those resins contain hydrophilic groups such as hydroxyl group, carboxylic acid group, carboxylic acid salt group in the molecule, and therefore have a high water absorption ability. It is preferred for the water absorbing resin to have high water absorption ability of at least 100 g/g as deionized water.

Those water absorbing resins can be used alone or as a mixture of two more same or different kinds of resins having different particle sizes.

The water absorbing resin powder has an average particle size of from 1 to 100 µm, and preferably from 5 to 30 µm.

The water absorbing resin is used in an amount of from 0 to 30% by weight, and preferably from 5 to 20% by weight, based on the weight of the rubbery adhesive.

Examples of the water-soluble polymer powder having an adhesiveness in the presence of water which can be used in the present invention include powders of polyacrylic acid, polyacrylic acid salt, polyacrylamide, polyethylene oxide, polyethylene imine, polyvinyl alcohol, polyvinyl chloride, polyvinyl pyrolidone, carboxyvinyl polymer, methyl cellulose, carboxymethyl cellulose, and hydroxyethyl cellulose. Those powder can be used alone or as a mixture of two or more same or different kinds of powder having different particle sizes.

The water absorbing polymer powder has an average particle size of from 1 to 100 µm, and preferably from 5 to 30 µm.

The water absorbing polymer powder is used in an amount of from 0 to 30% by weight, and preferably from 5 to 20% by weight, based on the weight of the rubbery adhesive.

The transdermal therapeutic system according to the present invention can be used in any optional form such as a tape preparation, and a patch type adhesive preparation.

Figure 2:
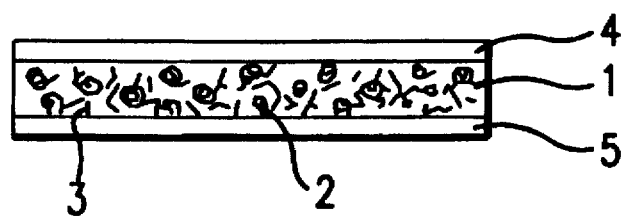
FIG. 2 is a cross-sectional view of the tape preparation according to the present invention.

FIG. 1 is a view explaining a layer obtained by applying a dispersion to a base fabric or a release paper in a tape preparation and FIG. 2 is a cross-sectional view of the tape preparation. In those Figures, 1 is a adhesive layer, 2 is microcapsules, 3 is a water absorbing resin powder, 4 is a base fabric, and 5 is a release paper.

The tape preparation can be produced by the following method. The rubbery adhesive comprising a rubber adhesive component, a tackifier, and a plasticizer is dissolved in a volatile organic solvent, the microcapsule 2 containing drugs and comprising a water-soluble wall material, and the water-insoluble, rubber- and rubber solvent-insoluble water absorbing resin powder 3 are dispersed in the solution obtained above, the resulting dispersion is applied to the base fabric 4 or the release paper 5, the organic solvent is volatilized to form the adhesive layer 1, in which the microcapsule 2 and the water absorbing resin powder 3 are dispersed, and the release paper 5 or the base fabric 4 is laminated on the adhesive layer 1, respectively.

Figure 3:
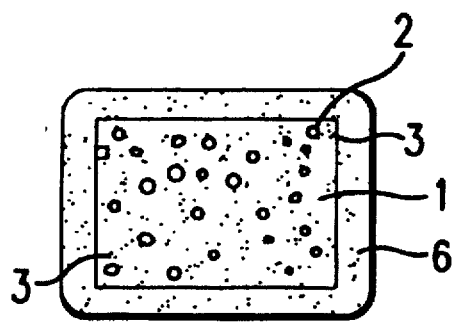
FIG. 3 is an explanatory view of a adhesive layer in one embodiment of a patch type adhesive preparation according to the present invention.
Figure 4:
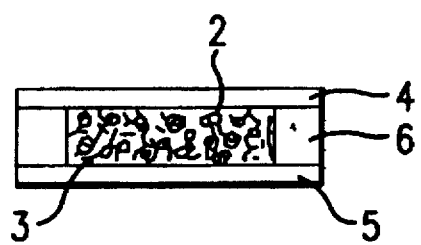
FIG. 4 is a cross-sectional view of the patch type adhesive preparation according to the present invention.
Figure 5:
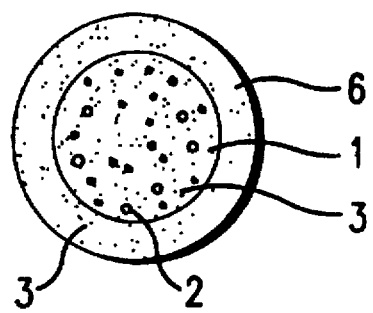
FIG. 5 is an explanatory view of the adhesive layer in another embodiment of the patch type adhesive preparation according to the present invention.
Figure 6:
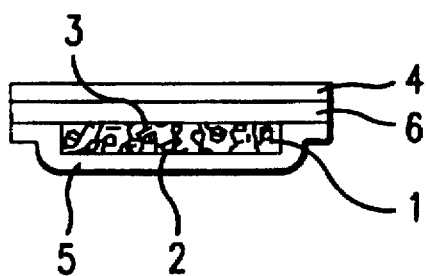
FIG. 6 is a cross-sectional view of further another embodiment of the patch type adhesive preparation according to the present invention.

FIGS. 3 and 4 show another embodiment of the patch type adhesive preparation, and FIGS. 5 and 6 show further another embodiment of the patch type adhesive preparation. In those patch adhesive preparations, the adhesive can be prepared in the same manner as in the tape preparation that the rubbery adhesive comprising the rubber adhesive component, the tackifier, and the plasticizer is dissolved in a volatile organic solvent, and that the microcapsule 2 containing drugs and comprising the water-soluble wall material 2, and the water-soluble, rubber- and rubber solvent-soluble, water absorbing resins powder 3 are dispersed in the solution obtained above.

The patch type adhesive preparation can be prepared by the following manner. The adhesive is applied to a part such as a central portion of the base fabric 4 or the release paper 5 to form the adhesive layer 1 having the microcapsule 2 and the water absorbing resin powder 3 dispersed therein, and the adhesive layer 6 which does not contain microcapsules is applied to the remaining portion, such as the circumferential portion of the base fabric 4 or the release paper 5, as shown in FIGS. 3 and 4. Alternatively, the adhesive layer which does not contain the microcapsules is formed on the base fabric 4 or the release paper 5, and the adhesive layer containing the microcapsule 2 and the water absorbing resin powder 3 dispersed therein is then laminated on the adhesive layer 6, as shown in FIGS. 5 and 6.

The adhesive can be applied by any coating method such as hot pressing method (calendar coating), hot melt method (hot melt coating), or solution coating. When the wall thickness of the microcapsule is small, the calendar coating and the hot melt coating involve the destruction of particles. Therefore, when the microcapsules having a small wall thickness are used, the solution coating is preferably employed. A solvent that can be used in the solution coating is preferably a solvent having a high dissolution property of natural rubber and synthetic rubbers, and the examples thereof include toluene, n-hexane, isohexane, cyclohexane, and a volatile oil for rubber.

The base fabric that can be used in the present invention is woven fabrics or non-woven fabrics, such as polyvinyl chloride films, polyester films, polyolefin films, laminated films of polyvinyl chloride films and polyester films, polyester films, polypropylene films, or rayon films; films obtained by hot welding the non-woven fabrics on the polyester films; or the like.

The present invention is described in more detail with reference to the following Examples, but it should be understood that the invention is not construed as being limited thereto unless otherwise indicated, all parts, percents, ratios, and the like are by weight.

EXAMPLE 1

Preparation of Microcapsules

250 Parts of a 5% polyvinyl alcohol aqueous solution, 250 parts of 5% carboxymethyl cellulose aqueous solution, 80 parts of flurbiprofen, and 50 parts of sorbitan sesquioleate were mixed with stirring to form o/w type emulsion. Temperature of the emulsion was raised to 40° C., and 250 parts of a 2.5% sodium chloride were gradually added thereto. The resulting mixture was cooled to 10° C., and 20 parts of a 50% glutaraldehyde were added thereto. The resulting mixture was stirred for 15 hours, was heated to 40° C., and was further stirred for 3 hours. The mixture was washed, filtered off, and spray dried. Microcapsules thus obtained had a concentration of a core material of 87%, a concentration of a drug (flurbiprofen) contained of 47.1%, and an average particle size of 16 µm.

Production of Transdermal Therapeutic System

30 Parts of a styrene-isoprene-styrene block copolymer, 10 parts of a polyisobutylene, 20 parts of liquid paraffin, and 30 parts of a tackifier (ESCORETS 5300) were dissolved in 350 parts of n-hexane.

3 Parts of the microcapsules obtained above, 5 parts of 100 mesh pass starch-polyacrylic acid graft copolymer, and 5 parts of 100 mesh pass polyacrylic acid powder (HIVISWAKOGEL) were dispersed in the adhesive solution obtained above. The resulting dispersion was coated on a release paper, and heated to evaporate n-hexane. A vinyl chloride film was laminated on the coating layer to obtain a transdermal therapeutic system.

EXAMPLE 2

Preparation of Microcapsule (I)

20 Parts of crotamiton, 20 parts of butylene glycol, and 10 parts of ethynyl estradiol were dispersed and emulsified in 30 parts of a 10% gelatin aqueous solution to form an o/w type emulsion. 30 Parts of a 10% gum arabic aqueous solution were added to the emulsion, followed by stirring for about 20 minutes. 200 Parts of 40° C. hot water were added to the mixture, and pH of the resulting mixture was adjusted to 4 to 4.3 with 10% acetic acid. After formation of a sol, the sol was cooled to 5° C. to form a gel. 1 Part of 30% formalin was added to the gel, and 10% sodium hydroxide was added droplet thereto to adjust the pH to 9. The mixture was gradually heated and stirred at 50° C. for about 1 hour. The mixture was washed with water, filtered off, and spray dried to obtain spherical microcapsules having a concentration of a core material of 89%, a concentration of a drug (ethynyl estradiol) contained of 12.7%, and an average particle size of 13 µm.

Preparation of Microcapsule (II) 15 parts of clotamiton, 20 parts of butylene glycol, and 15 parts of ethynyl estradiol were dissolved in 40 parts of a 12.5% gelatin aqueous solution to form an o/w type emulsion. 30 Parts of a 10% gum arabic aqueous solution were added to the emulsion, followed by mixing for about 20 minutes. After adding 200 parts of 40° C. hot water to the mixture, pH of the resulting mixture was adjusted with a 10% acetic acid to 4 to 4.3 to form a sol. The sol was cooled to 5° C. to form a gel. 1 Part of 30% formalin was added to the gel, and 10% sodium hydroxide was added dropwise thereto to adjust the pH to 9. The mixture was gradually heated, and stirred at 50° C. for about 1 hour. The resulting mixture was washed, filtered off, and spray dried to obtain spherical microcapsules having a concentration of a core material of 76%, a concentration of drug (ethynyl estradiol) of 15.1%, and an average particle size of 16 µm.

Production of Transdermal Therapeutic system

25 Parts of a styrene-isoprene-styrene block copolymer, 15 parts of polyisobutylene, 25 parts of liquid paraffin, and 25 parts of a tackifier (ESCORET 5300) were mixed with and dissolved in 340 parts of n-hexane to prepare a adhesive solution. 2 Parts of the microcapsule (I) obtained above, 3 parts of the microcapsule (II) obtained above, and 7 parts of 100 mesh pass starch-polyacrylic acid salt graft copolymer (SUNWET M1000) were mixed with and dispersed in the adhesive solution. The resulting dispersion was coated on a release paper, and heated to evaporate n-hexane to form a adhesive layer. A vinyl chloride film was laminated on the surface of the adhesive layer to obtain a transdermal therapeutic system.

What is claimed is:

1. A release controlled transdermal therapeutic system comprising a rubber adhesive, microcapsules and a water-insoluble, rubber- and rubber solvent-insoluble, water absorbing resin powder;

wherein the microcapsules comprise a water-soluble wall material, and the microcapsules encapsulate drugs as core material; and wherein the resin power is selected from the group consisting of starch-polyacrylic acid salt graft copolymers, crosslinked polyacrylic acid salts, acrylic acid-vinyl alcohol copolymers, polyoxyethyleneoxide crosslinked products, and crosslinked isobutylene-maleic acid salt copolymers; and wherein the microcapsules and the resin powder are dispersed in the rubber adhesive.

2. A release controlled transdermal therapeutic system comprising a rubber adhesive, microcapsules comprising a water-soluble wall material and encapsulating drugs as core material, a water-insoluble, rubber- and rubber solvent-insoluble, water absorbing resin powder, and a rubber- and rubber solvent-insoluble, water-soluble polymer powder having adhesive properties in the presence of moisture, wherein the microcapsules, resin powder, and the polymer powder are dispersed in the rubber adhesive.

3. The release controlled transdermal therapeutic system as claimed in claim 1, wherein the rubbery adhesive comprises at least one rubber adhesive component selected from the group consisting of natural rubbers, isoprene rubbers, isobutylene rubbers, styrene copolymer rubbers, silicone rubbers and acrylic rubber, at least one tackifier selected from the group consisting of petroleum resins, rosins, hydrogenated rosins, ester gums, terpene resins, modified terpene resins, coumarone-indene resins, petroleum cracking fractions, aromatic hydrocarbon resins, styrene resins and isoprene resins; and at least one plasticizer selected from the group consisting of polybutenes, low molecular weight polyisobutylenes, vaseline, lanolin, liquid paraffin, higher fatty acid esters, vegetable oils, and animal oils.

4. The release controlled transdermal therapeutic system as claimed in claim 1, wherein the water absorbing resin powder has an average particle size of form 1 to 100 μm.

5. The release controlled transdermal therapeutic system as claimed in claim 1, wherein the microcapsules contain at least one oily drug which does not dissolve the wall material.

6. The release controlled transdermal therapeutic system as claimed in claim 1, wherein the wall material comprises at least one member selected from the group consisting of gelatin, gum arabic, polyvinyl alcohol, and carboxymethyl cellulose.

7. The release controlled transdermal therapeutic system as claimed in claim 1, wherein the microcapsule particles comprise at least two kinds of microcapsules having different wall thicknesses.

8. The release controlled transdermal therapeutic system as claimed in claim 1, wherein the microcapsules have an average particle size of from 1 to 100 μm.

9. The release controlled transdermal therapeutic system as claimed in claim 1, wherein the microcapsules further contain an absorption accelerator as a core material, comprising at least one selected from the group consisting of aliphatic alcohols having 10 to 22 carbon atoms, aliphatic carboxylic acids having 9 to 22 carbon atoms, aliphatic amines, aliphatic carboxylic acid esters having 10 to 22 carbon atoms N-alkyl lactam, crotamiton, and monoterpene compounds.

10. A tape preparation which is obtained by the steps of:

dissolving a rubber adhesive comprising a rubber adhesive component, a tackifier, and a plasticizer in a volatile organic solvent to prepare a rubbery adhesive solution, dispersing microcapsules containing drugs, and a water-insoluble, rubber- and rubber solvent-insoluble, water absorbing resin powder into the rubber adhesive solution to prepare a dispersion, applying the dispersion to a base fabric or a release paper, volatilizing the organic solvent from the resulting coating to prepare a rubber adhesive layer, laminating a release paper or a base fabric on the surface of the rubber adhesive layer.

11. A patch adhesive preparation which is obtained by the steps of:

dissolving a rubber adhesive comprising a rubber adhesive component, a tackifier, and a plasticizer in a volatile organic solvent to prepare a rubber adhesive solution, dispersing microcapsules drugs, and a water-insoluble, rubber- and rubber solvent-insoluble, water absorbing resin powder in the rubber adhesive solution to prepare a dispersion, applying the resulting dispersion to a part of a base fabric or a release paper, and laminating thus coated fabric or paper with a rubber adhesive, which does not contain microcapsules or coating a rubber adhesive, which does not contain microcapsules, on uncoated part of the fabric or paper.

* * * * *